(12) United States Patent
Yoon et al.

(10) Patent No.: US 9,238,055 B2
(45) Date of Patent: Jan. 19, 2016

(54) PEPTIDE BONE FORMING PEPTIDE 4 FOR PROMOTING OSTEOGENESIS OR VASCULARIZATION AND USE THEREOF

(71) Applicant: Chonnam National University Hospital, Gwangju (KR)

(72) Inventors: Taek Rim Yoon, Gwangju (KR); Hyung Keun Kim, Gwangju (KR); Ji Hyun Kim, Gwangju (KR); Myung Ho Jeong, Gwangju (KR)

(73) Assignee: Chonnam National University Hospital, Gwangju (KR)

( * ) Notice: Subject to any disclaimer, the term of this patent is extended or adjusted under 35 U.S.C. 154(b) by 0 days.

(21) Appl. No.: 14/153,191

(22) Filed: Jan. 13, 2014

(65) Prior Publication Data

US 2014/0200174 A1    Jul. 17, 2014

Related U.S. Application Data

(62) Division of application No. 13/486,035, filed on Jun. 1, 2012, now abandoned.

(30) Foreign Application Priority Data

Jun. 3, 2011    (KR) .......................... 10-2011-0054179

(51) Int. Cl.
*A61K 38/10*    (2006.01)
*C07K 7/08*    (2006.01)
*C07K 14/51*    (2006.01)

(52) U.S. Cl.
CPC ................. *A61K 38/10* (2013.01); *C07K 14/51* (2013.01)

(58) Field of Classification Search
CPC ................................. A61K 38/10; C07K 7/08
USPC .......... 514/16.4, 17.7, 1.9, 21.5; 530/326, 300
See application file for complete search history.

(56) References Cited

U.S. PATENT DOCUMENTS

| 6,407,060 B1 * | 6/2002 | Charette et al. ................ 514/8.8 |
| 2004/0067505 A1 * | 4/2004 | Alvarez et al. .................... 435/6 |
| 2011/0195906 A1 | 8/2011 | Yoon et al. |

FOREIGN PATENT DOCUMENTS

| WO | 00/47114 A1 | 8/2000 |
| WO | 2009/139525 A1 | 11/2009 |
| WO | 2009/154330 A1 | 12/2009 |

OTHER PUBLICATIONS

European Search Report for EP12793200.2 (PCT/KR2012/004346).

* cited by examiner

*Primary Examiner* — Julie Ha
(74) *Attorney, Agent, or Firm* — The PL Law Group, PLLC

(57) ABSTRACT

Disclosed are a peptide for promoting osteogenesis and vascularization, and the use thereof. The peptide has a low molecular weight so that it can be economically produced. In addition, it promotes osteoblastic differentiation, thus inducing osteogenesis. Further, the peptide can promote the expression of VEGF, resulting in vascularization. Accordingly, the peptide is useful for the delay of the onset of ischemic diseases and the therapy of ischemic diseases.

5 Claims, 7 Drawing Sheets

SEQ ID No. 1: Phe-Phe-Lys-Ala-Thr-Glu-Val-His-
Phe-Arg-Ser-Ile-Arg-Ser-Thr
(F-F-K-A-T-E-V-H-F-R-S-I-R-S-T)

Interpreted sequence
1-letter code: FFKATEVHFRSIRST
3-letter code: Phe-Phe-Lys-Ala-Thr-Glu-Val-His-Phe-Arg-Ser-Ile-
Arg-Ser-Thr (SEQ ID No. 1)

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: peptide for promoting osteoporosis or
      vascularization

<400> SEQUENCE: 1

Phe Phe Lys Ala Thr Glu Val His Phe Arg Ser Ile Arg Ser Thr
1               5                   10                  15
```

PEPTIDE BONE FORMING PEPTIDE 4 FOR PROMOTING OSTEOGENESIS OR VASCULARIZATION AND USE THEREOF

CROSS REFERENCE TO RELATED APPLICATION

This application is a divisional application of application Ser. No. 13/486,035, filed on Jun. 1, 2012, which claims the benefit of Korean Patent Application No. 10-2011-0054179, filed on Jun. 3, 2011, which are incorporated herein by reference in its entirety.

BACKGROUND

1. Technical Field

The present invention relates to a peptide useful for promoting osteoporosis or vascularization and the use thereof.

2. Description of the Related Art

Bones constitute part of the endoskeleton which physically supports the body, and play an important role in maintaining the blood calcium level. In a normal state, bones exhibit dynamic homeostasis in which both bone resorption and formation actively proceed in metabolic balance. The disruption of the balance between bone resorption and formation with a shift towards bone resorption causes a decrease in bone mineral density or bone mass and bone strength, leading to osteoporosis.

Osteoporosis is a bone disease characterized by the high risk of fracture upon receiving just a slight impact as a result of weakened bones. Other representative bone diseases are osteoarthritis and bone defects. Osteoarthritis, also known as degenerative arthritis, is characterized by a local degenerative change in the joint as a result of the breakdown and loss of cartilage. Bone defects may form in many sites of the body, predominantly because of acute trauma with the accompaniment of bone matrix loss, acute trauma with the accompaniment of surgical bone loss, chronic infection with the accompaniment of bone resection, and chronic nonunion with the accompaniment of segmental defects.

The market associated with bone disease around the world amounts to approximately 130 billion dollars and it is expected to continuously expand in size. Thus, research institutes and pharmaceutical companies have made tremendous investments in the development of medicines for bone diseases.

Medicines currently used for osteoporosis include bisphosphonates (alendroate, etidronate, etc.), hormonal agents (raloxifene), vitamin D agents, calcitonin agents and calcium agents. Recently, the parathyroid hormone agent FORTEO™ has been commercially available and has an ability to form new bones.

However, bisphosphonates have a problem associated with the uptake thereof in that because bisphosphonates are absorbed at a very low rate and cause erosion of the esophagus, the patients must take them together with a sufficient amount of water and sit upright for a time after the uptake of the medication. Hormonal agents are required to be taken over the entire lifespan of the patients and the administration thereof over the long term may cause side effects such as breast cancer, uterine cancer, and thrombosis. Vitamin D agents are very expensive, and their pharmaceutical efficacy is not reliable. Calcitonin agents are also expensive and have a problem associated with the administration thereof. Calcium agents do not engender significant side effects, but are limited to prophylactic effects rather than therapeutic effects.

The parathyroid hormone agent, FORTEO™, which has recently been commercialized, can induce bone formation and thus has an advantage over conventional drugs that work to prevent bone resorption. However, it suffers from the disadvantages of being administered by daily injection over a long period of time and being very expensive. There is therefore the need for a novel medication and method that can increase bone mass and improve bone quality to substantially reduce the risk of fracture, thus being applicable to the treatment of osteoporosis.

Ischemic diseases are caused by locally restricting the blood supply as a result of various pathological abnormalities in the blood vessels, with resultant damage or malfunction of tissues. Blood supply through vessels is essential for wound healing or tissue regeneration. Vascular diseases, such as arteriosclerosis, myocardial infarction, and angina pectoris are caused by restricted blood flow.

Vascular therapy is used to treat diseases by generating vessels. Vascular endothelial growth factor (VEGF) is already used as a therapeutic for severe ischemia. Other vasculogenic or angiogenic factors such as fibroblast growth factor (FGF), epidermal growth factor (EGF) and platelet-derived endothelial growth factor (PDEGF) have also been studied for purposes of clinical use. However, these factors are proteins and so are difficult to separate and purify. In addition, they are too expensive for clinical application.

Leading to the present invention, intensive and thorough research into the treatment of bone diseases and ischemic diseases, conducted by the present inventors under the background, resulted in the finding that BFP 4 (bone forming peptide 4) can be economically synthesized and has the activity of promoting osteogenesis and vascularization.

SUMMARY

It is an aspect of the present invention to provide an isolated peptide useful for the promotion of osteogenesis or vascularization, including an amino acid sequence of SEQ ID NO: 1.

The peptide may be an isolated and/or substantially purified peptide.

It is another aspect of the present invention to provide an isolated polynucleotide encoding the peptide.

It is a further aspect of the present invention to provide a recombinant vector carrying the polynucleotide.

It is still a further aspect of the present invention to provide a pharmaceutical composition for the prevention or treatment of a bone disease or an ischemic disease, including the peptide, a polynucleotide encoding the peptide, or a recombinant vector carrying the polynucleotide as an active ingredient.

It is still yet another aspect of the present invention to provide a method of preventing or treating a disease selected from the group consisting of a bone disease, an ischemic disease and a combination thereof, the method including administering a subject with a therapeutically or pharmaceutically effective amount of a peptide comprising an amino acid sequence of SEQ ID NO: 1.

DETAILED DESCRIPTION

Figure 1A:
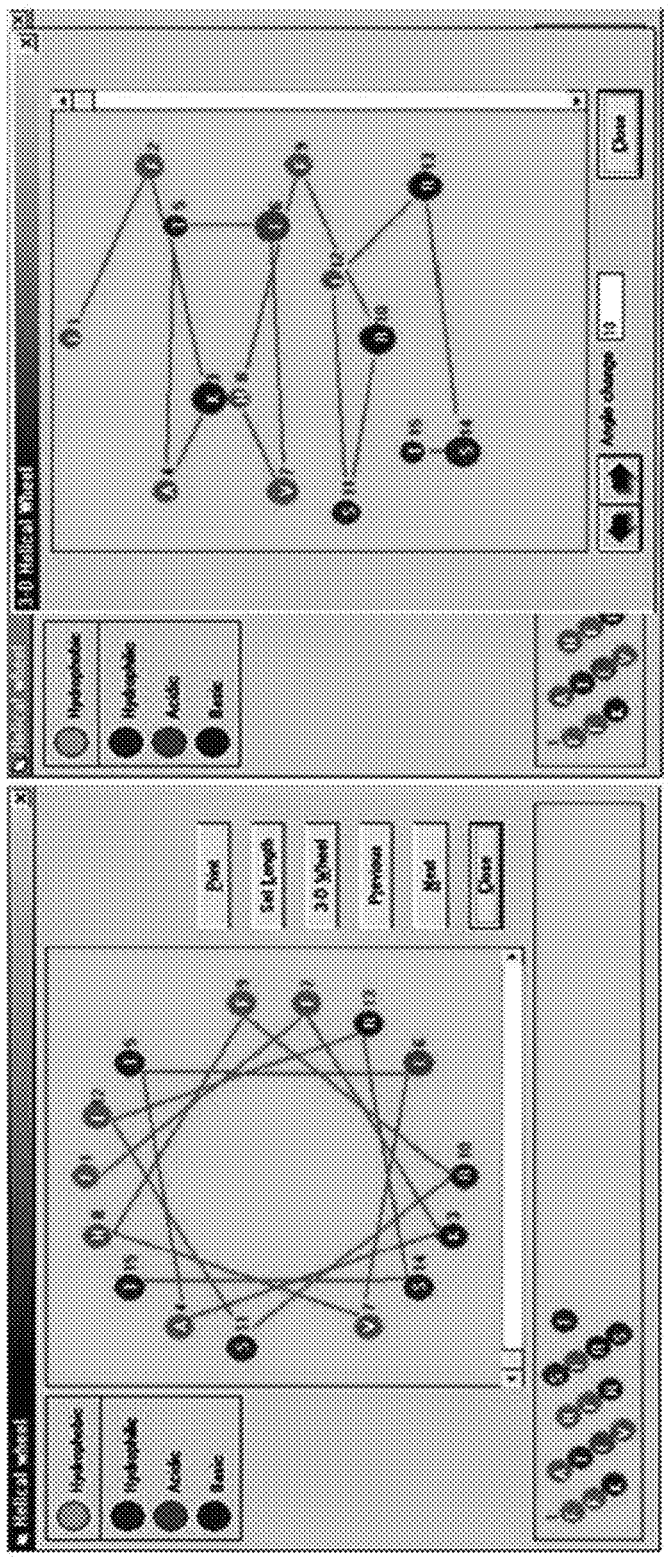
FIGS. 1A and 1B are a diagram showing the amino acid sequence, and structure (FIG. 1A) and net charge of BFP 4 (FIG. 1B).
Figure 1B:
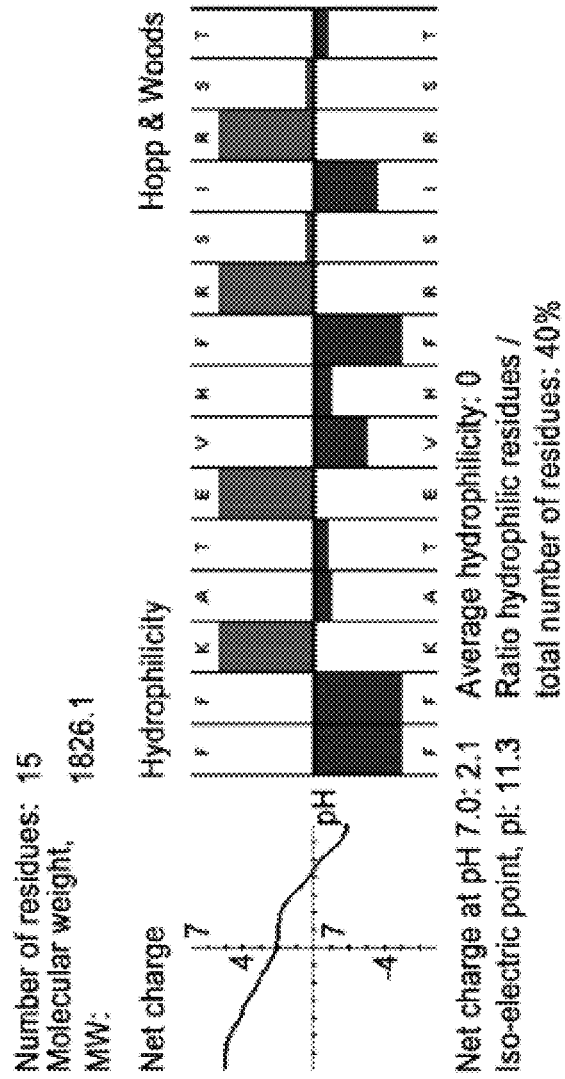

Exemplary embodiments of the present invention will be described in detail below with reference to the accompanying drawings. However, the exemplary embodiments of the present invention described herein are merely examples, and the scope of the present invention is not limited thereto.

In accordance with one aspect thereof, the present invention provides a peptide for promoting osteogenesis or vascularization, including the amino acid sequence of SEQ ID NO: 1.

SEQ ID NO: 1: Phe-Phe-Lys-Ala-Thr-Glu-Val-His-Phe-Arg-Ser-Ile-Arg-Ser-Thr

As used herein, the term "osteogenesis" is intended to refer to the process of laying down new bone material, including the formation of bone matrix by osteoblasts and the mineralization thereof.

The term "vascularization," as used herein, is intended to refer to the physical process of blood vessel formation, that is, the generation of new blood vessels into cells, tissues or organs, including both the de novo production of endothelial cells (vasculogenesis) and the growth of new blood vessels from pre-existing ones (angiogenesis).

As used herein, the term "promoting osteogenesis or vascularization" or grammatical variations thereof means bringing about osteogenesis or vascularization within a short time, including the induction of osteogenesis and vascularization.

By the term "peptide," as used herein, is meant a short polymer of amino acids linked by peptide bonds. All of the amino acids may have an L- or D-configuration. The peptide of the present invention includes the amino acid sequence of SEQ ID NO: 1. Variations in the peptides including fusion with other amino acids or peptides are within the scope of the present invention so long as it has the activity of promoting osteogenesis or vascularization.

The amino acid useful in the present invention may include a naturally occurring amino acid, a synthetic amino acid, and an amino acid analog and an amino acid mimic, which act like naturally occurring amino acids. The term "naturally occurring amino acid" means an amino acid encoded by genetic code. The amino acid analog is a compound which has hydrogen atoms, a carboxyl group, an amino group and an α carbon atom linked to an R group, with a modification given to the R group (e.g., norleucine) or the peptide backbone. The term "amino acid mimic" means a chemical compound which differs from amino acids in chemical structure, but acts like a naturally occurring amino acid.

Also, homologues of the peptide of the present invention fall within the scope of the present invention. The term "homologues", as used herein, means peptides which exhibit substantially identical physiological activity to that of the peptide of SEQ ID NO: 1. The homologues exhibiting "identical physiological activity" may be peptides that share an amino acid sequence homology of at least 60%, for example, at least 70% and for another example, at least 90% with the peptide of SEQ ID NO: 1.

The amino acid sequence of SEQ ID NO: 1 may be derived from BMP7, and for example, from the prodomain of Bone morphogenetic protein 7 (BMP7). Bone morphogenetic proteins (BMPs) are known as factors capable of inducing ossification, but exist in a trace amount in nature. BMPs have high-molecular weights and the recombinant preparation thereof is very expensive. In addition, many restrictions are put on the use of BMPs as medications in terms of physical properties and administration due to the proteinous properties thereof. In contrast, the peptide of the present invention is a low-molecular weight compound including 15 amino acids and can be economically produced. Also in terms of function, the peptide of the present invention exhibits an osteogenic effect identical to or higher than that of BMP7.

The peptide of the present invention may promote osteoblast differentiation or VEGF expression.

In an embodiment, the peptide of the present invention may be a peptide having the activity of promoting osteogenesis and vascularization.

Figure 2:
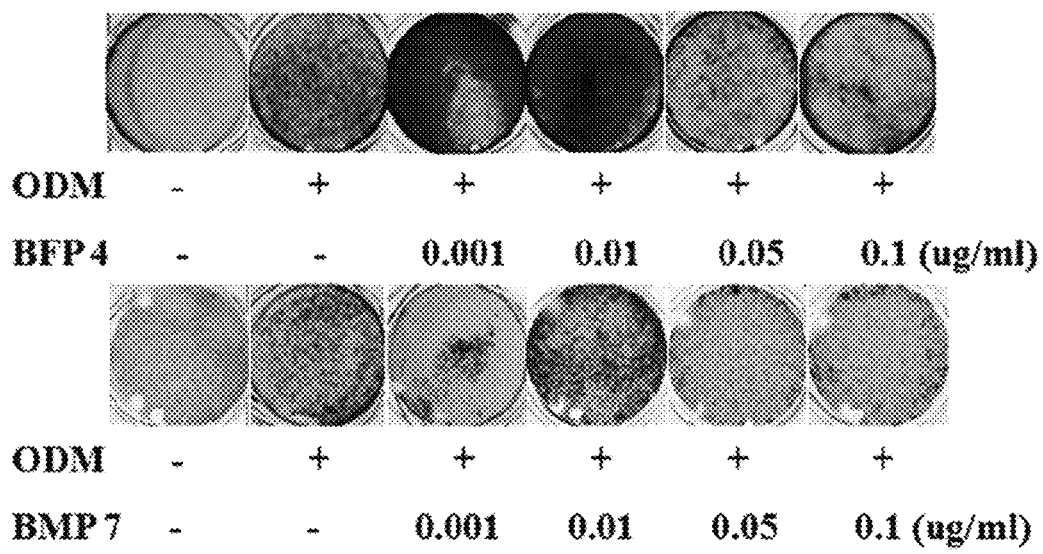
FIG. 2 is of photographs showing the ability of BFP 4 to promote osteoblastic differentiation, as analyzed by Alizarin red staining.
Figure 8:
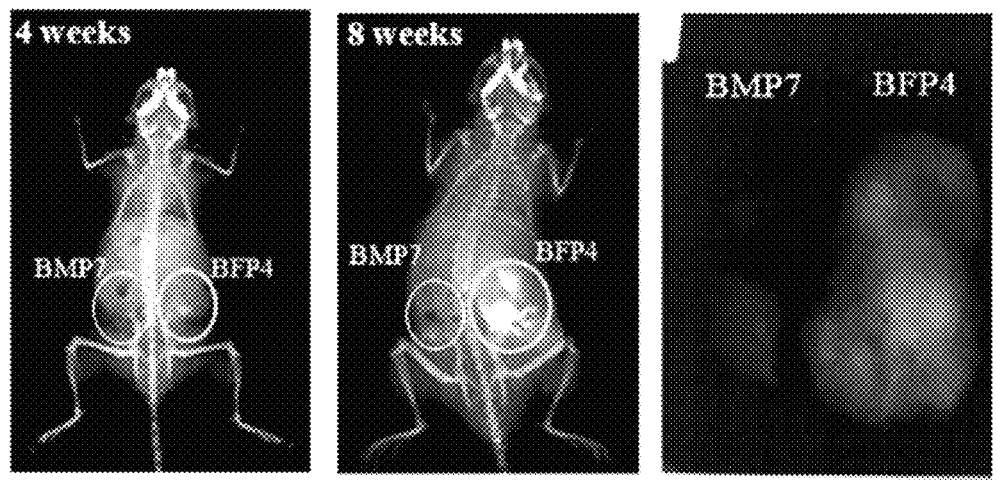
FIG. 8 is of X-ray photographs showing the BFP 4-induced osteogenesis in transplanted regions of mice.

In an experiment in which the differentiation of osteoblast cells was examined, the peptide of the present invention was found to promote osteoblastic differentiation at higher levels than did BMP7, as measured by Alizarin Red staining (FIG. 2). Also, an animal test with mice showed that even a greater extent of bone formation was achieved at sites treated with the peptide of the present invention than with BMP7 (FIG. 8). Therefore, the peptide of the present invention can be useful for the prevention and treatment of bone diseases.

Figure 9:
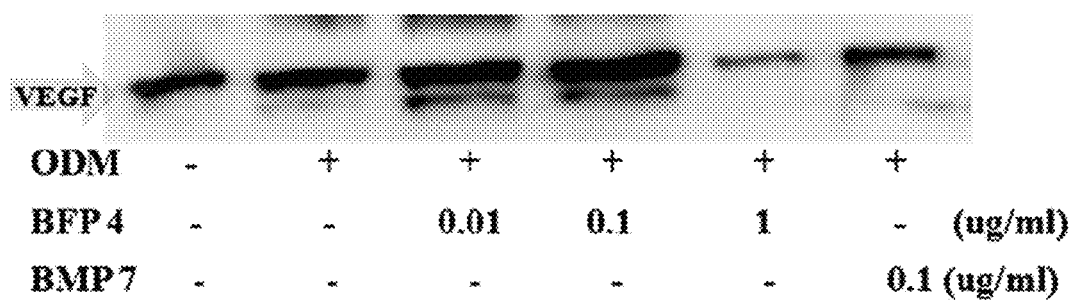
FIG. 9 is a photograph showing the BFP 4-induced expression of VEGF.
Figure 10:
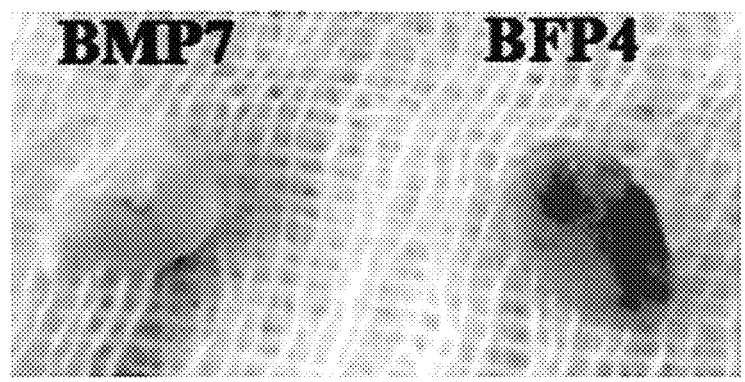
FIG. 10 is a photograph showing the BFP 4-induced vascularization in Matrigel transplanted into an animal.

The expression of Vascular endothelial growth factor (VEGF), known as a potent factor involved in vascularization, stimulates the formation of new blood vessels. In an example of the present invention, a higher level of VEGF was expressed by the peptide of the present invention than by BMP7 (FIG. 9). An animal test of mice showed that the peptide of the present invention induced the formation of new blood vessels in matrigel (FIG. 10). Accordingly, the peptide of the present invention can be useful for the prevention and treatment of ischemic diseases.

The peptide of the present invention may be prepared using a well-known peptide synthesis method or by culturing transformed host cells. In the latter case, typically, a polynucleotide encoding the peptide is introduced into an expression vector which is then transformed into a host cell, and the transformant is cultured to produce the peptide. To culture the transformant, any appropriate method known in the art may be used.

In accordance with another aspect thereof, the present invention provides a polynucleotide encoding the peptide of the present invention, and a recombinant vector carrying the same.

As used herein, the term "polynucleotide" refers to a polymer composed of many nucleotide monomers covalently bonded in a chain, as exemplified by DNA (deoxyribonucleic acid) or RNA (ribonucleic acid). The polynucleotide of the present invention includes a polynucleotide encoding the peptide of the present invention.

In the polynucleotide of the present invention, various modifications may be made in the encoding region provided that they do not change the amino acid sequence of the polypeptide expressed from the coding region, due to codon degeneracy or in consideration of the codons preferred by the organism in which they are to be expressed, and various modifications or alterations may be introduced even in regions other than the coding region so long as they have no influence on the expression of the gene. That is to say, the polynucleotide of the present invention may be modified at one or more nucleic acid bases by substitution, deletion, insertion or a combination thereof as long as the resulting polynucleotides encode functionally equivalent polypeptides, and they are also within the scope of the present invention.

The recombinant vector of the present invention is a means for expressing the peptide of the present invention within a host cell. Any expression vector such as a plasmid vector, a cosmid vector, a bacteriophage vector, and so on may be used so long as it is known for an expression vector in the art. The vector may be readily constructed by the artisan of ordinary skill using a well-known DNA recombination technique.

In accordance with a further aspect thereof, the present invention provides a pharmaceutical composition for the prophylaxis or therapy of a bone disease or an ischemic disease, including as an active ingredient the polypeptide of the present invention, a polynucleotide encoding the polypeptide, or a recombinant vector carrying the polynucleotide.

In accordance with still a further aspect thereof, the present invention provides a method for the prophylaxis or therapy of a bone disease or an ischemic disease, including administering the pharmaceutical composition to a subject which has been attacked with or is likely to be attacked with the bone disease or the ischemic disease.

As used herein, the term "prevention" refers to any measure taken in order to suppress or delay the onset of bone diseases or ischemic diseases by administering the pharmaceutical composition of an embodiment of the present invention. The term "treatment," as used herein, refers to any measure taken in order to improve or beneficially alter symptoms of bone diseases or ischemic diseases by administering the pharmaceutical composition of an embodiment of the present invention.

The term "subject," as used herein, refers to any animal including humans, which has been attacked with or is likely to be attacked with the bone disease or ischemic disease. The bone disease may be selected from the group consisting of osteoporosis, osteoarthritis, bone fracture, osteogenesis imperfect and a combination thereof. The ischemic disease may be one selected from the group consisting of ischemic necrosis, ischemic cerebrovascular diseases, ischemic renal diseases, ischemic lung diseases, ischemic diseases of the limbs, ischemic heart diseases, apoplexy, cerebral infarction, myocardial infarction, ischemic heart failure, angina pectoris, obstructive arteriosclerosis and a combination thereof.

So long as it allows the pharmaceutical composition of the embodiment of the present invention to reach tissues or cells of interest (e.g. bone-defected site), any administration route may be taken. Depending on the purposes of administration, the pharmaceutical composition of the embodiment of the present invention may be administered directly or indirectly via intraperitoneal, intravenous, intramuscular, subcutaneous, interdermal, oral, intrapulmonary, intrarectal, or intracellular routes. In this context, the pharmaceutical composition of the embodiment of the present invention may be administered by means of any device capable of transporting an active ingredient into target cells.

The pharmaceutical composition of an embodiment of the present invention may further include a pharmaceutically acceptable vehicle. When containing a pharmaceutically acceptable vehicle, the pharmaceutical composition of an embodiment of the present invention may exist in various oral or non-oral dosage forms. In this regard, the pharmaceutical composition of an embodiment of the present invention may be formulated in combination with diluents or an excipient such as a filler, a thickener, a binder, a wetting agent, a disintegrant, a surfactant, etc. Solid preparations intended for oral administration may take the form of tablets, pills, powders, granules, capsules, and the like. In regards to these solid agents, the peptide of an embodiment of the present invention may be formulated in combination with at least one excipient such as starch, calcium carbonate, sucrose, lactose, or gelatin. Liquid preparations intended for oral administration include suspensions, internal use solutions, emulsions, syrups, and the like. In addition to a simple diluent such as water or liquid paraffin, various excipients, such as wetting agents, sweetening agents, aromatics, preservatives, and the like may be contained in the liquid preparations. Also, the pharmaceutical composition of the embodiment of the present invention may be administered via a non-oral route. For this, sterile aqueous solutions, non-aqueous solvents, suspensions, emulsions, lyophilizates, suppositories, and the like may be used. Injectable propylene glycol, polyethylene glycol, vegetable oils such as olive oil, and esters such as ethyl oleate may be suitable for non-aqueous solvents and suspensions. The basic materials of suppositories include Witepsol, macrogol, Tween 61, cacao butter, laurin butter, and glycerogelatin.

The dosage form of the pharmaceutical composition of the present invention may be selected from the group consisting of a tablet, a pill, a powder, a granule, a capsule, a suspension, an internal use solution, an emulsion, a syrup, a sterile aqueous solution, a non-aqueous solution, a suspension, a lyophilizate, and a suppository.

The pharmaceutical composition of the present invention is administered in a therapeutically or pharmaceutically effective amount. The term "therapeutically or pharmaceutically effective amount," as used herein, is intended to refer to a sufficient amount of the pharmaceutical composition to treat a disease, at a reasonable benefit/risk ratio applicable to any medical treatment. The effective amount may vary depending on various factors including the severity of the disease being treated, the patient's age and sex, drug activity, sensitivity to drugs, the time of administration, the route of administration, the rate of excretion, the period of time of treatment, the co-administration of drugs, and other parameters well known in the art.

For treating bone diseases or ischemic diseases, the pharmaceutical composition of the present invention may be used in combination with surgery, hormones, drugs, and/or biological reaction regulators.

A better understanding of the present invention may be obtained through the following examples which are set forth to illustrate, but are not to be construed as limiting the present invention.

Example 1

Synthesis of BFP 4

The peptide having the amino acid sequence of SEQ ID NO: 1 can be artificially synthesized using a well-known method. The synthesis of the peptide was entrusted to Peptron Co., Ltd (Korea). The peptide having the amino acid sequence of SEQ ID NO: 1 was named BFP 4 (bone forming peptide 4).

Phe-Phe-Lys-Ala-Thr-Glu-Val-His-Phe-Arg-Ser-Ile-Arg-Ser-Thr (SEQ ID NO: 1)

Analysis with a commercial program showed that BFP 4 is composed of 15 amino acid residues with a molecular weight of 1826.1 and has an alpha-helix structure as illustrated in FIG. 1A.

Example 2

Preparation of Osteoblast Cells and Osteogenic Differentiation Medium

For use as osteoblast cells in this example, mesenchymal stem cells isolated from Balb/c mouse bone marrow stromal cells were seeded at a density of $1 \times 10^4$ cells in a DMEM (Dulbecco's Modified Eagle Medium) supplemented with 10% FBS and incubated at 37° C. for about 3 days in a 5% $CO_2$ atmosphere.

An osteogenic differentiation medium (ODM) was prepared by supplementing DMEM with 50 µg/mL ascorbic acid, $10^{-8}$ M dexamethasone and 10 mM beta-glycophosphate.

Example 3

Assay of BFP 4 for Ability to Promote Osteoblastic Differentiation

Because calcium is deposited when the mesenchymal stem cells differentiate into osteoblasts, the degree of osteoblastic differentiation was analyzed by measuring mineralization with Alizarin red staining. That is, the greater advance in osteoblastic differentiation produced a wider region positive to Alizarin red. After the cells in the osteogenic differentiation medium were treated with BFP 4 in the presence of Alizarin Red, the staining of Alizarin red was monitored to determine the degree of osteoblastic differentiation. In this regard, the mesenchymal cells were transferred into an osteogenic differentiation medium and incubated for three days. Thereafter, BFP 4 or BMP7 was added in concentrations of 0.001 µg/mL, 0.01 µg/mL, 0.05 µg/mL, and 0.1 µg/mL to the medium, followed by incubation for an additional 2 days. Subsequently, the mesenchymal stem cells were fixed for one hour with ice-cooled 70% ethanol and stained for about 10 min with Alizarin red-S to analyze the degree of deposition of calcium. The results are shown in FIG. 2.

As can be seen in FIG. 2, the most intensive staining was detected in the cells treated with BFP 4 at a concentration of 0.01 µg/mL. Particularly, BFP 4 according to the present invention was found to produce more intensive colors than did BMP7 (FIG. 2). These data indicate that activity for osteoblastic differentiation of BFP 4 is more potent than that of BMP7.

Example 4

Assay for Cytotoxicity of BFP 4

Figure 3:
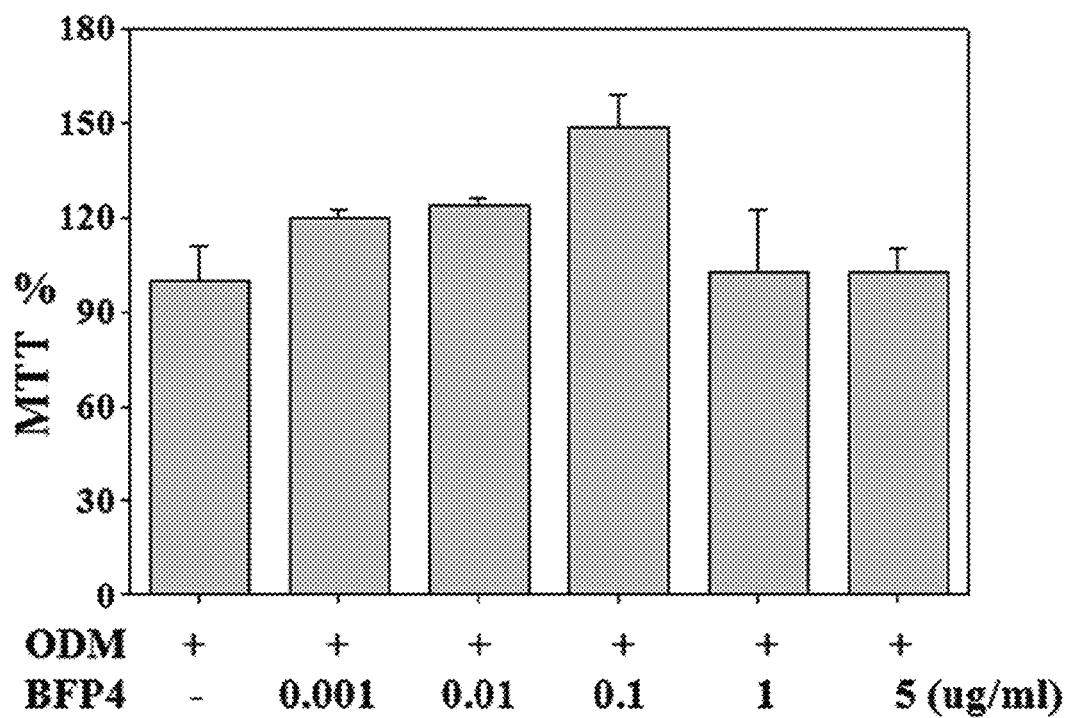
FIG. 3 is a graph showing the non-cytotoxicity of BFP 4.

At concentrations effective for calcium deposition, BFP 4 was analyzed for cytotoxicity. The results are shown in FIG. 3. In this context, MTT ((3-(4,5-Dimethylthiazol-2-yl)-2,5-diphenyltetrazolium bromide, a yellow tetrazole) assay was performed using an MTT Cell Proliferation Assay Kit (Cayman Chemical) according to the instructions of the manufacturer.

As seen in FIG. 3, no cytotoxicity was detected at concentrations of BFP 4 which are effective for promoting osteogenic differentiation.

Example 5

Assay of BFP 4 for Ability to Increase ALP Activity and Calcium Level

During osteoblastic differentiation, alkaline phosphatase (ALP), a marker enzyme characteristic of osteoblasts, and calcium were quantitatively analyzed using a DALP-250 QuantiChrom Alkaline Phosphatase Assay Kit (Gentaur) and a DICA-500 QuantiChrom Calcium Assay Kit (Gentaur), respectively. The results are depicted in FIGS. 4A and 4B.

Figure 4A:
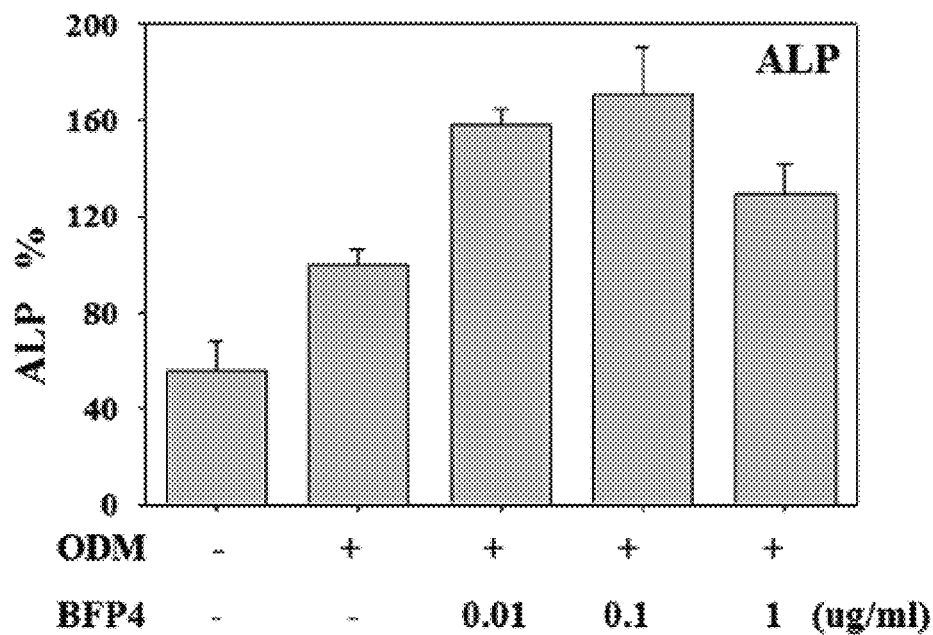
FIGS. 4A and 4B are of graphs showing BFP 4-induced increases in ALP activity and calcium level, respectively.
Figure 4B:
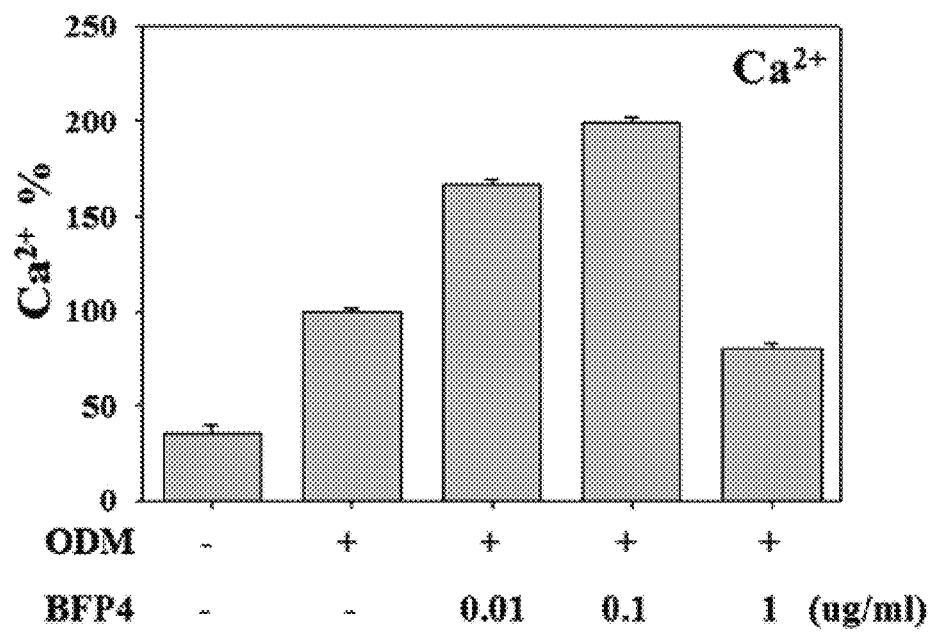

As can be seen in FIGS. 4A and 4B, both the activity of ALP and the concentration of calcium were significantly increased at BFP 4 concentrations of 0.01 µg/mL and 0.1 µg/mL.

Example 6

Assay for BFP 4-Induced Osteoblast-Specific Gene Expression

Figure 5:
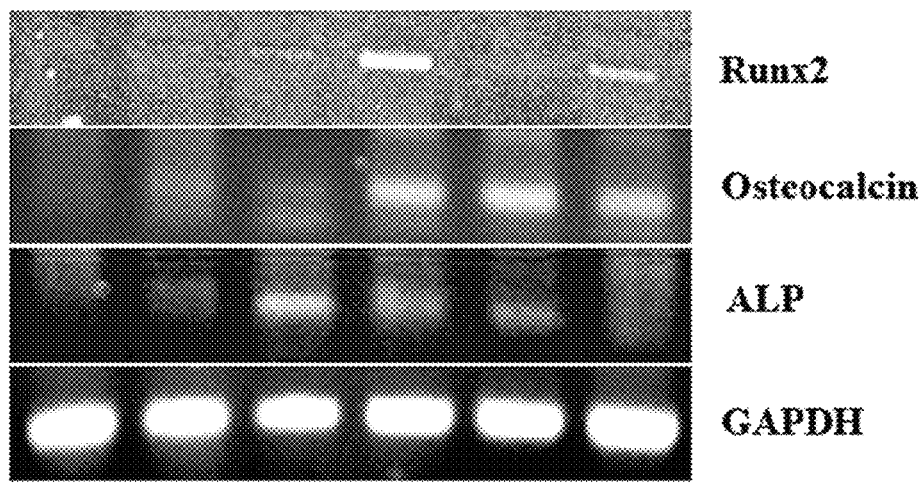
FIG. 5 is a photograph showing the BFP 4-induced expression of runx2, osteocalcin and ALP genes by western blot.

The ability of BFP 4 to induce the expression of runx2, osteocalcin and alkaline phosphatase genes, which are marker genes characteristic of osteoblasts, was assayed. The results are shown in FIG. 5. In this regard, RNA was isolated from the cells treated with the peptide and reverse transcribed into DNA which was then used as a template for PCR. Electrophoresis of the PCR products determined the expression levels of the marker genes.

As shown in FIG. 5, BFP 4 induced expression of the osteoblast-specific genes.

Example 7

Assay of BFP 4-Induced Cell Surface Marker Expression During Osteoblastic Differentiation The effect of BFP 4 on the expression of CD44 and CD51, surface proteins characteristically emerging during differentiation from mesenchymal stem cells into osteoblasts, was measured using FACS. The results are shown in FIG. 6.

Figure 6:
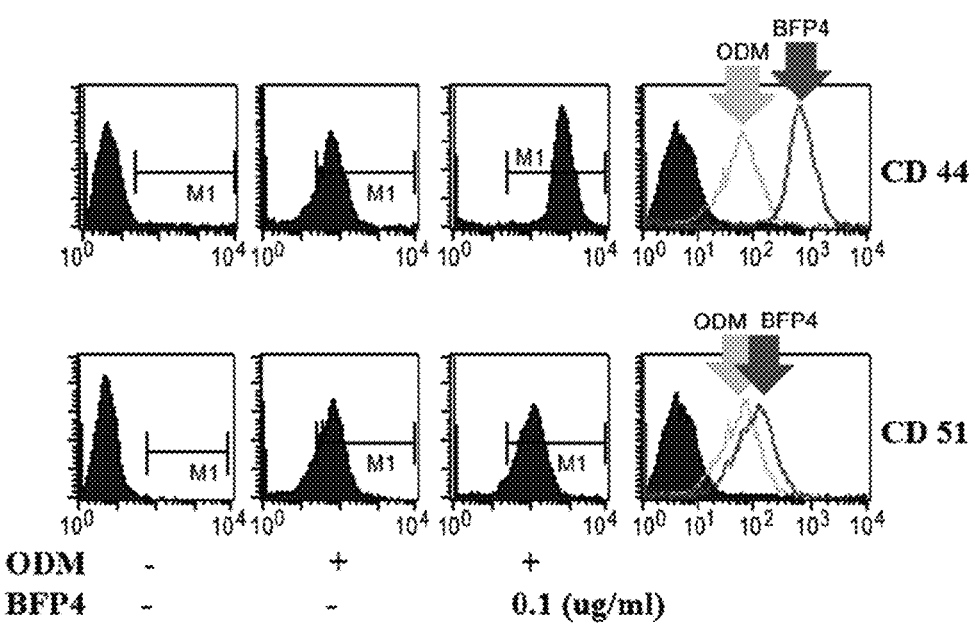
FIG. 6 is of graphs showing the BFP 4-induced expression of cell surface markers (CD44 and CD51) associated with osteoblastic differentiation, as analyzed by FACS.

As seen in FIG. 6, when BFP 4 was added to the osteogenic differentiation medium, the cell surface marker CD44 was expressed at a high level in the mesenchymal cells which were undergoing osteoblastic differentiation. Particularly, a peak in the expression level of CD44 was detected at a BFP 4 concentration of 0.1 µg/mL. Also, CD51 was expressed at higher levels in the presence of BFP 4 during the osteoblastic differentiation (FIG. 6).

Example 8

Assay for BFP 4-Induced Expression of Cell Surface Markers CD44 and CD51

Figure 7:
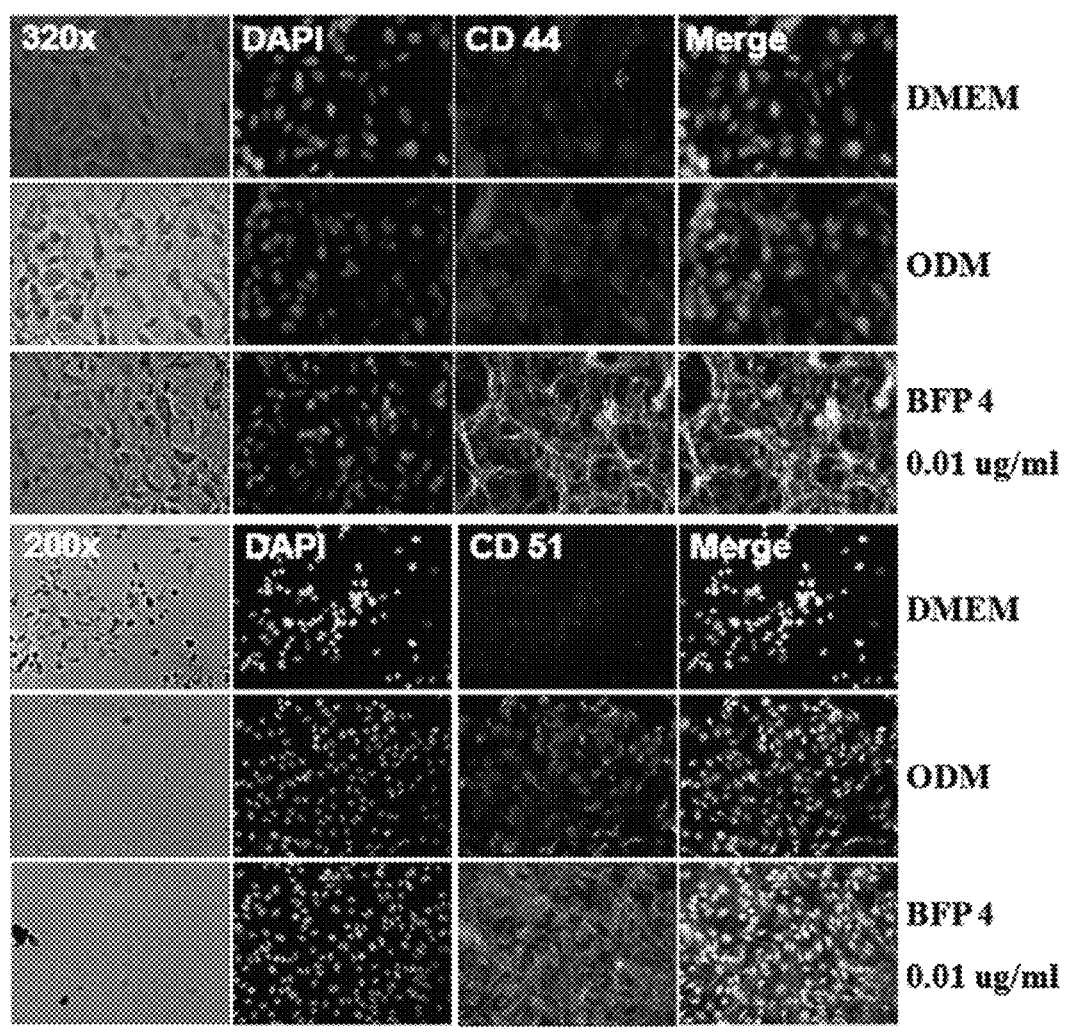
FIG. 7 is of fluorescence microphotographs showing the BFP 4-induced expression of CD44 and CD51.

The BFP 4-induced expression of the cell surface markers CD44 and CD51 was observed using a fluorescence microscope, and the results are given in FIG. 7. In this regard, DAPI (4',6-diamidino-2-phenylindole) staining was performed to ascertain the viability of the cells during osteoblastic differentiation, and anti-CD44 or CD51 antibodies which appear when they bind to the antigens, were used for fluorescence analysis.

As can be seen in FIG. 7, both CD44 and CD51 were expressed in the cells. Higher expression levels of CD44 and CD51 were observed in the osteogenic differentiation medium in the presence of BFP 4.

Example 9

In Vivo Assay of BFP 4 for Ability to Promote Osteogenesis In Vivo

An animal test with mice (n=6) was performed to examine the ability of BFP 4 to promote osteogenesis in vivo. First, mesenchymal stem cells were treated twice with ODM over two days to induce osteoblastic differentiation. Upon the second treatment with ODM, BMP7 or BFP 4 was added to the cells, followed by incubation for 24 hours. Cells were harvested and transplanted in the same number into the back of the mice, with collagen serving as a scaffold. Using X-rays, bone formation was examined 4 and 8 weeks after the transplantation. The results are given in FIG. 8.

As can be seen in the X-ray photographs of FIG. 8, four weeks after transplantation, new bones were formed in the region treated with BFP 4. In addition, as seen in the photographs taken 8 weeks after transplantation, a significantly higher extent of bone formation was achieved in the region treated with BFP 4 than that treated with BMP7. These experimental results imply that BFP 4 has higher activity of promoting osteoblastic differentiation compared to the conventional factor BMP7, and can be useful for the prevention and treatment of bone diseases.

Example 10

Assay for BFP 4-Induced VEGF Expression

To examine the effect of BFP 4 on vascularization, BFP 4 was assayed for its ability to induce VEGF expression. In this regard, proteins were isolated from the cells treated with the peptide and subjected to electrophoresis before measurement using an anti-VEGF antibody.

As seen in FIG. 9, the expression of VEGF was induced by BFP 4 and to a higher level than by BMP7.

Example 11

In Vivo Assay for Vascularization of BFP 4

To examine the ability of BFP 4 to form new blood vessels in vivo, a mouse animal test was performed using Matrigel. In this context, cells were treated with the peptide and mixed well with Matrigel before transplantation into the back of the mice. Eight weeks after the transplantation, the Matrigel was detached from the mouse back which was then observed with regard to the formation of new blood vessels.

As shown in FIG. 10, blood vessels were newly formed in the Matrigel 8 weeks after transplantation. Particularly, more vascularization was induced by BFP4 than by BMP7

As shown above, the peptide for promoting osteogenesis in accordance with the present invention has a low molecular weight so that it can be economically synthesized. In addition, the peptide of the present invention can promote osteoblastic differentiation, thus inducing osteogenesis. Hence, the peptide of the present invention is useful in the prevention or treatment of bone diseases.

Also, the peptide for promoting vascularization in accordance with the present invention can induce the expression of VEGF, resulting in vascularization. Therefore, the peptide of the present invention is applicable to the prevention or treatment of ischemic diseases.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of delaying onset of or treating an ischemic disease in a subject in need thereof, the method comprising: administering the subject with a therapeutically or pharmaceutically effective amount of a peptide consisting of the amino acid sequence of SEQ ID NO: 1.

2. The method of claim 1, wherein the ischemic disease is selected from the group consisting of ischemic necrosis, ischemic cerebrovascular disease, ischemic renal diseases, ischemic lung diseases, ischemic diseases of limbs, ischemic heart diseases, apoplexy, cerebral infarction, myocardial infarction, ischemic heart failure, obstructive arteriosclerosis, and a combination thereof.

3. The method of claim 1, wherein the subject is a human.

4. The method of claim 1, wherein the method is of delaying the onset of the disease.

5. The method of claim 1, wherein the method is of treating the disease.

\* \* \* \* \*